(12) United States Patent
Liu et al.

(10) Patent No.: US 9,638,558 B2
(45) Date of Patent: May 2, 2017

(54) IN SITU SPACING-CORRECTING HEAT PULSE SENSOR AND METHOD FOR MEASURING SAP FLOW OR WATER FLUX

(71) Applicant: China Agricultural University, Beijing (CN)

(72) Inventors: Gang Liu, Beijing (CN); Minmin Wen, Beijing (CN); Robert Horton, Ames, IA (US); Ruiqi Ren, Beijing (CN); BingCheng Si, Saskatoon (CA); Jianping Wang, Shandong (CN); Baoguo Li, Beijing (CN)

(73) Assignee: China Agricultural University, Beijing (CN)

( * ) Notice: Subject to any disclaimer, the term of this patent is extended or adjusted under 35 U.S.C. 154(b) by 0 days.

(21) Appl. No.: 14/588,986

(22) Filed: Jan. 5, 2015

(65) Prior Publication Data
US 2017/0030751 A1 Feb. 2, 2017

(30) Foreign Application Priority Data
Mar. 5, 2014 (CN) .......................... 2014 1 0078861

(51) Int. Cl.
*G01F 1/684* (2006.01)
*G01N 33/00* (2006.01)
*G01N 33/24* (2006.01)

(52) U.S. Cl.
CPC ......... *G01F 1/684* (2013.01); *G01N 33/0098* (2013.01); *G01N 33/24* (2013.01)

(58) Field of Classification Search
CPC ..... G01F 1/684; G01N 33/0098; G01N 33/24

USPC ........................................... 73/204
See application file for complete search history.

(56) References Cited

U.S. PATENT DOCUMENTS

| | | | | | |
|---|---|---|---|---|---|
| 5,223,405 | A | * | 6/1993 | Howell | G01N 1/04 422/404 |
| 5,263,359 | A | * | 11/1993 | Mookherjee | G01N 33/0098 73/23.2 |
| 5,269,183 | A | * | 12/1993 | Van Bavel | G01F 1/68 73/204.22 |
| 5,337,604 | A | * | 8/1994 | Van Bavel | G01F 1/68 73/204.22 |

(Continued)

FOREIGN PATENT DOCUMENTS

| | | | | |
|---|---|---|---|---|
| CN | 201429578 Y | * | 3/2010 | |
| CN | 103913481 A | * | 7/2014 | ............. G01F 1/684 |

*Primary Examiner* — Francis Gray (57) ABSTRACT

In situ spacing-correcting heat pulse sensor for measuring sap flow or water flux includes: a holder; a temperature probe or two (sometimes there will be more than two) mounted on the holder; and a heating probe mounted on the holder; wherein two or three thermometric elements are provided axially in the same temperature probe, all the thermometric elements are connected to a data collector, a heating wire is mounted in the heating probe, and the heating wire is connected to a power supply. A measuring method thereof is also provided. In practice, by arranging at least two thermometric elements in each temperature probe, measurement errors of sap flow in plant or soil water flux caused by factors such as deflection of the temperature probe or the heating probe are reduced. Furthermore, the sensor is simple in structure, low in cost, convenient in utilization, and accurate in measurement.

9 Claims, 3 Drawing Sheets (56) References Cited

U.S. PATENT DOCUMENTS

2008/0025366 A1* 1/2008 McBurney ............. G01N 27/18
                                                     374/44
2015/0369786 A1* 12/2015 De Groot ............. A01G 25/167
                                                     47/66.6

* cited by examiner

IN SITU SPACING-CORRECTING HEAT PULSE SENSOR AND METHOD FOR MEASURING SAP FLOW OR WATER FLUX

CROSS REFERENCE OF RELATED APPLICATION

The present invention claims priority under 35 U.S.C. 119(a-d) to CN 201410078861.1, filed Mar. 5, 2014.

BACKGROUND OF THE PRESENT INVENTION

Field of Invention

The present invention relates to a technical field of measurement, and more particularly to an in situ spacing-correcting heat pulse sensor based on both inline deflections and non-inline deflections for measuring sap flow or water flux and a measuring method thereof.

Description of Related Works

1. Theoretical Background of Soil Water Flux Measurement

Figure 1:
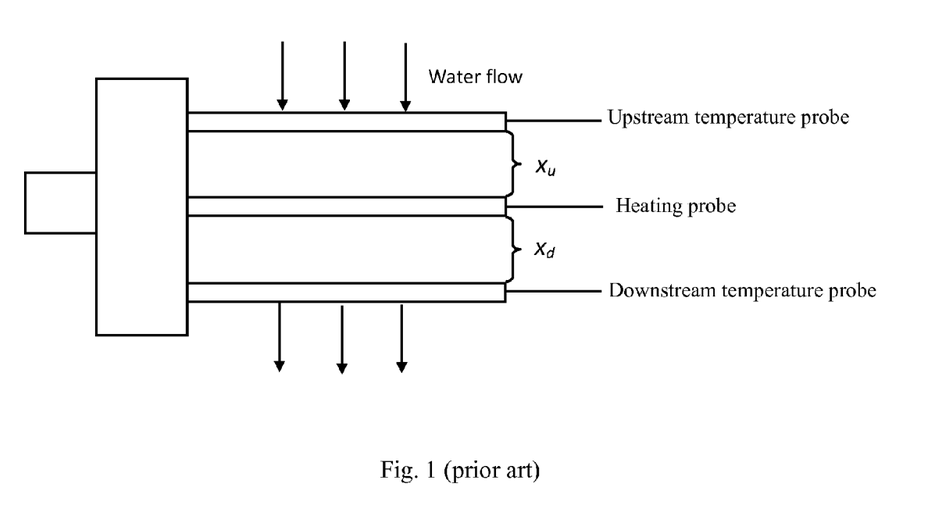
FIG. 1 is a sketch view of a conventional heat pulse sensor for measuring sap flow or water flux at a working state according to prior arts.

A device for measuring soil water flux with the heat pulse method comprises three probes (with higher thermal conductivity) in parallel, wherein a heating probe is in the middle, and the other two are temperature probes with thermometric elements, which are arranged on both sides of the heating probe. The temperature probes include an upstream temperature probe and a downstream temperature probe as shown in FIG. 1. The soil water flux can be estimated by maximum difference of the temperatures recorded by the upstream and the downstream temperature probes.

For water flow with constant velocity in a homogenous and infinite medium, the heat conduction equation is:

$$\frac{\partial T}{\partial t} = \alpha \left( \frac{\partial^2 T}{\partial x^2} + \frac{\partial^2 T}{\partial y^2} \right) - V \frac{\partial T}{\partial x} \tag{1}$$

wherein, T is temperature (° C.), t is time (s), $\alpha$ represents thermal diffusivity (m s$^{-2}$), and x and y represent spatial coordinates.

$$V = \theta_w V_w C_w / C = J C_w / C \tag{2}$$

wherein, $\theta_w$ represents water content, $V_w$ represents water flow rate (m s$^{-1}$), $C_w$ represents volume heat capacity of water (J m$^{-3}$ °C.$^{-1}$) and C represents volume heat capacity of soil (J m$^{-3}$ °C.$^{-1}$). The heat conduction equation illustrates the relationship between the thermal diffusivity and V. With a known thermal diffusivity, V is able to be calculated with measured data. Then the water flux J is able to be calculated according to the equation 2.

For a homogeneous medium, when heated with an infinite linear source for a heating time of $t_0$, temperature change of the temperature probe satisfies:

$$T(x, y, t) = \begin{cases} \frac{q}{4\pi\lambda} \int_0^t s^{-1} \exp\left[-\frac{(x-Vs)^2 + y^2}{4\alpha s}\right] ds & 0 < t < t_0 \\ \frac{q}{4\pi\lambda} \int_{t-t_0}^t s^{-1} \exp\left[-\frac{(x-Vs)^2 + y^2}{4\alpha s}\right] ds & t > t_0 \end{cases} \tag{3}$$

wherein, s represents dummy variable for evaluating integral, q is heat released by a unit length of the linear heat source within a unit time (J m$^{-1}$ s$^{-1}$).

Conventional methods for calculating soil water flux:

a) Maximum Dimensionless Temperature Difference Method, i.e. MDTD Method

The maximum dimensionless temperature difference (DTD) is defined as:

$$DTD = \frac{4\pi\lambda(T_d - T_u)}{q} \tag{4}$$

wherein $T_d$ is the temperature increment of the downstream temperature probe, $T_u$ is the temperature increment of the upstream temperature probe. When reaching the maximum value, the DTD is marked as MDTD.

$$MDTD = \int_{t_m-t_0}^{t_m} s^{-1} \left\{ \exp\left[-\frac{(x_d - Vs)^2}{4\alpha s}\right] - \exp\left[-\frac{(x_u + Vs)^2}{4\alpha s}\right] \right\} ds \tag{5}$$

wherein $t_m$ is the time when the DTD reaches the maximum value, $t_0$ is the heating time, $x_u$ is the spacing between the upstream temperature probe and the heating probe (actually, the measured $x_u$ is the spacing between the temperature element in the upstream temperature probe and the heating probe), and $x_u$ is the spacing between the downstream temperature probe and the heat source (also as the upstream, the measured $x_u$ is the spacing between the temperature element in the downstream temperature probe and the heat source). After obtaining the MDTD value by measurement, V is able to be calculated according to the calculated thermal diffusivity, and then the water flux is obtained according to the equation 2.

b) Heat Ratio Method

It is introduced that the water flux can be calculated according to the ratio of the temperature increments of the two temperature probes. Accordingly, a calculation equation for water flux J is:

$$J = \frac{2\lambda}{(x_d + x_u)C_w} \ln\left(\frac{T_d}{T_u}\right) = \frac{C(x_d - x_u)}{2C_w(t - (t_0/2))}; t > t_0/2 \tag{6}$$

c) Maximum Temperature Time Method

Supposing that the time when the measured temperature of upstream temperature probe reaches the maximum temperature is $t_u$, and the time when the measured temperature of temperature probe reaches the maximum temperature is t*, then the relationship is:

$$V^2 = \frac{4\alpha}{t_0} \ln\left(\frac{t_* - t_0}{t_*}\right) + \frac{x_*^2}{(t_* - t_0)t_*} \tag{7}$$

where t* can be $t_d$ or $t_u$ respectively and correspondingly, x* can be $x_d$ or $x_u$ respectively.

V is obtained according to the above equations. Combined with the thermal diffusivity and the equation 2, the water flux J can be obtained.

2. Theoretical Background of Sap Flow Measurement

Basic principles of a heat pulse method for measuring sap flow in trees are similar to those for measuring soil water flux. Probes thereof are basically the same as the probes for measuring soil water flux, but differ in the probe spacings and the probe lengths. Initial spacings of the probes for measuring soil water flux, $x_u$ and $x_d$, are approximately the same, wherein the initial spacings are about 6 mm. For the sap flow measurement, great differences exist between different methods. Several popular methods for measuring sap flow density (SFD) (m³ m⁻² s⁻¹) are mainly introduced here.

For an ideal instantaneous line source, temperature changes thereof satisfy:

$$\Delta T = \frac{q}{4\pi\lambda t}\exp\left(-\frac{\rho c}{4\lambda t}((x-V_h t)^2 + y^2)\right) \quad (8)$$

wherein the coordinate of the heat source is (0, 0), $\Delta T$ is the temperature change at the point (x, y) after applying a heat pulse with a strength of q (m s⁻¹), $V_h$ is heat pulse velocity (m s⁻¹). Unlike the soil, the tree has different axial and tangential heat conductivities. Therefore:

$$\Delta T = \begin{cases} \frac{q}{4\pi\sqrt{\lambda_{ax}\lambda_{tg}}}\int_0^t \frac{1}{t}\exp\left[-\frac{\rho c}{4t}\left(\frac{(x-V_h t)^2}{\lambda_{ax}} + \frac{y^2}{\lambda_{tg}}\right)\right]dt & 0 < t < t_0 \\ \frac{q}{4\pi\sqrt{\lambda_{ax}\lambda_{tg}}}\int_{t-t_0}^t \frac{1}{t}\exp\left[-\frac{\rho c}{4t}\left(\frac{(x-V_h t)^2}{\lambda_{ax}} + \frac{y^2}{\lambda_{tg}}\right)\right]dt & t > t_0 \end{cases} \quad (9)$$

wherein $\lambda_{ax}$ is the axial heat conductivity of the wood, $\lambda_{tg}$ is the tangential heat conductivity of the wood.

The SFD can be calculated according to the following equation:

$$SFD = \frac{\rho_d}{\rho_s}\left(MC + \frac{c_{dw}}{c_s}\right)V_h \quad (10)$$

wherein, MC is the water content of the wood (weight of water over weight of dry wood), $c_{dw}$ is the specific heat of the wood (J kg⁻¹ K⁻¹), $\rho_d$ is the density of the dry wood (kg m⁻³), $\rho_s$ is the density of the sap (kg m⁻³), which is usually considered as the density of water, and $c_s$ is the specific heat of the sap flow (J kg⁻¹ K⁻¹), which is usually considered as the specific heat of water.

a) Compensation Heat Pulse Method, i.e. CHP Method $$V_h = \frac{x_d - x_u}{2t_c} \quad (11)$$

wherein, $t_c$ is a time when the temperature measured by upstream and the downstream temperature probes reach the same value. According to the method, differ from the measurement of the soil water flux, $x_d$ and $x_u$ are different initially.

b) $T_{max}$ Method:

In the $T_{max}$ method, only one temperature probe, the downstream temperature probe, is utilized. The temperature detected by the temperature probe reaches the maximum value at time $t_d$:

$$V_h = \sqrt{\frac{4\alpha_{ax}}{t_0}\ln\left(1 - \frac{t_0}{t_d}\right) + \frac{x_d^2}{t_d(t_d - t_0)}} \quad (12)$$

$$\alpha_{ax} = \frac{x_d^2}{4t_d}\frac{t_0}{(t_d - t_0)}\left[\ln\left(\frac{t_d}{t_d - t_0}\right)\right]^{-1} \quad (13)$$

wherein $\alpha_{ax}$ represents axial thermal diffusivity of wood when the sap flow is 0.

c) Heat Ratio Method, i.e. HR Method

Calculation of the heat ratio method is based on that $x_d$ and $x_u$ are both equal. As a fact, $x_d$ and $x_u$ are easy to change. Therefore, the improved equation is:

$$V_h = \frac{4\alpha_{ax}t\ln(\Delta T_d/\Delta T_u) - x_d^2 + x_u^2}{2t(x_u - x_d)} \quad (14)$$

wherein t is the time when the ratio of the temperature change of downstream and upstream temperature probe ($\Delta T_d/\Delta T_u$) becomes a nearly invariable value (the average temperature ratio of measurements between 60 and 100 s can satisfy that). Some people use the median measurement time (80 s) or average solutions calculated for each t value used in the measurement series.

d) "Sap Flow+" Method

According to the method, for the upstream and downstream temperature probes, there is a horizontal temperature probe instead of the upstream temperature probe in some cases, wherein the spacing between the horizontal temperature probe and the heating probe is y. According to the equation 9, desired parameters can be obtained.

There are still many other methods for measuring sap flow in trees, without further introduction herein.

3. Calculation of Thermal Diffusivity α

Only when the sap or water flow rate is approximately 0 are the thermal diffusivity and the specific heat able to be accurately measured. Specific heat measurement is an approximate solution based on infinite linear heat source (ILS). When the linear heat source is infinite and heats continuously from 0 to $t_0$, given that the space between the heating probe and the temperature probe is r (it can be $x_u$ or $x_d$), the temperature increment can be calculated according to the following equation:

$$\Delta T(r, t) = \begin{cases} -\frac{q}{4\pi\alpha\rho c}Ei\left(\frac{-r^2}{4\alpha t}\right) & t < t_0 \\ -\frac{q}{4\pi\alpha\rho c}\left\{Ei\left[\frac{-r^2}{4\alpha(t-t_0)}\right] - Ei\left(\frac{-r^2}{4\alpha t}\right)\right\} & t > t_0 \end{cases} \quad (15)$$

wherein $\Delta T$ is the temperature change value (° C.), Ei(-x) is an exponential integral. According to the above equation, a time of $t_m$ is needed for the temperature to reach a maximum value, then α can be calculated according to equation 16.

$$\alpha = \frac{r^2}{4}\left\{\frac{1/(t_m - t_0) - 1/t_m}{\ln[t_m/(t_m - t_0)]}\right\} \quad (16)$$

wherein, $t_m$ is the corresponding time when the maximum temperature increment $\Delta T_m$ occurs.

Referring to the above introduction of the conventional technology, it is known that no matter which method is utilized for calculating sap or water flux, $x_u$ and $x_d$ are always the key factors. However, in practice, temperature probes of both sap flow measurement and soil water flux measurement are liable to deform under factors such as external force. For example, during the measurement of sap flow in trees, if pretreatments such as drilling holes are applied, the spacings between the temperature probes (actually the temperature elements) and heating probe is also liable to deviate from the original spacing because of technique defects. Besides, factors such as growth of the tree also matters. The above factors will finally lead to huge deviation of the result of sap flow measurement. During the measurement of soil water flux, due to impurities, such as stones and roots in soil, alternating freezing and thawing, distortion during installation, etc., the temperature probe or the heating probe may be deflect. All of the above factors can change $x_u$ and $x_d$, and finally lead to a huge difference between a calculated value and an actual measured value of the sap flow or soil water flux using heat pulse method.

SUMMARY OF THE PRESENT INVENTION

An object of the present invention is to accurately calculate an actual spacing between a temperature probe and a heating probe. (As a matter of fact, the measured spacing between temperature probe and heating probe is the spacing between the temperature element and the heating probe.)

Accordingly, in order to accomplish the above object, the present invention provides an in situ spacing-correcting heat pulse sensor based on both inline deflection and non-inline deflection (nonlinear deflection) for measuring sap flow or water flux, comprising:

a holder;

a temperature probe or two (sometimes there will be more than two) mounted on the holder; and a heating probe mounted on the holder;

wherein a first thermometric element (it can be thermistor, thermal couple or any other elements), a second thermometric or a third thermometric element are provided axially in the same temperature probe, the first and the second or the third thermometric elements are all connected to a data collector, a heating wire is mounted in the heating probe, the heating wire is connected to a power supply device.

Preferably, a ratio of the length to the diameter of the heating probe is larger than 25.

Preferably, an axial distance between two adjacent thermometric elements in the same temperature probes is big enough, in such a manner that positions of the first and the second (or the third, for non-inline (nonlinear) deflection) thermometric elements in one of the temperature probes satisfy that: a relative deviation of a temperature, detected by the first and the second (or the third, for non-inline (nonlinear) deflection) thermometric element arranged from a top or a bottom portion of the temperature probe, from a temperature detected at a middle position of the temperature probe, is less than 1%.

Preferably, a quantity of the temperature probe is no less than 1.

Preferably, the temperature probe and the heating probe are grouted onto the holder with a sealing material which is insulating and solidifiable.

Preferably, the sealing material is epoxy resin or all any other suitable materials with high thermal conductivity.

Preferably, the temperature probe and the heating probe are both hollow needle tubes made of stainless steel or other metal with high thermal conductivity.

A measuring method of the in situ spacing-correcting heat pulse sensor for measuring sap flow or water flux is also provided, comprising steps of:

a) respectively calculating the initial spacings between thermometric elements in a temperature probe and a heating probe;

b) when soil water flux or sap flow in a tree is 0 or approximately 0, inserting the temperature probe and the heating probe into the soil or pre-drilled holes in the tree, and sampling a first temperature-time response data;

c) for inline deflection, judging whether the temperature probe deflects inwards or outwards according to a difference between temperature changes of the two thermometric elements in the temperature probe, wherein if a time $t_{u,1}$ for the first temperature element 5 to reach a maximum value is longer than a time $t_{u,2}$ for the second temperature element 6 to reach a maximum value, the temperature probe deflected outwards; otherwise, the temperature probe deflected inwards and for non-inline deflection, directly executing a step d);

d) calculating the actual spacings between the thermometric elements and the heating probe after the temperature probe or the heating probe deflects, and calculating a thermal diffusivity;

e) sampling a second temperature-time response data when the sap flow in the trees or the soil water flux is not 0; and f) calculating the sap flow in the tree or the soil water flux according to parameters comprising the calculated actual spacings and times for temperatures of the two (for inline deflection) or three (for non-inline deflection) thermometric elements to reach maximum values, etc.

Preferably, the initial spacings between the thermometric elements in the temperature probe and the heating probe are calibrated with a material whose thermal conductivity and specific heat are known.

According to the present invention, the in situ spacing-correcting heat pulse sensor for measuring sap flow or soil water flux and the measuring method thereof is able to obtain the actual spacing between the temperature probe and the heating probe by the two or three thermometric elements in each of the temperature probes, and reduce measurement errors caused by factors such as deflection and inclination of the temperature probe or the heating probe. Furthermore, the sensor with simple structure is able to realize accurate measurements, and is economical and practical.

BRIEF DESCRIPTION OF THE DRAWINGS

These and other objectives, features, and advantages of the present invention will become apparent from the following detailed description, the accompanying drawings, and the appended claims.

Reference numbers: 1—heating probe, 2—first temperature probe, 3—second temperature probe, 4—heating wire, 5—first thermometric element, 6—second thermometric element, 7—third thermometric element, 8—fourth thermometric element, 9—holder, 10—fifth thermometric element, 11—sixth thermometric element.

DETAILED DESCRIPTION OF THE PREFERRED EMBODIMENT

Referring to the drawings and preferred embodiments, the present invention is further illustrated. One skilled in the art will understand that the embodiment of the present invention as shown in the drawings and described above is exemplary only and not intended to be limiting.

Figure 2:
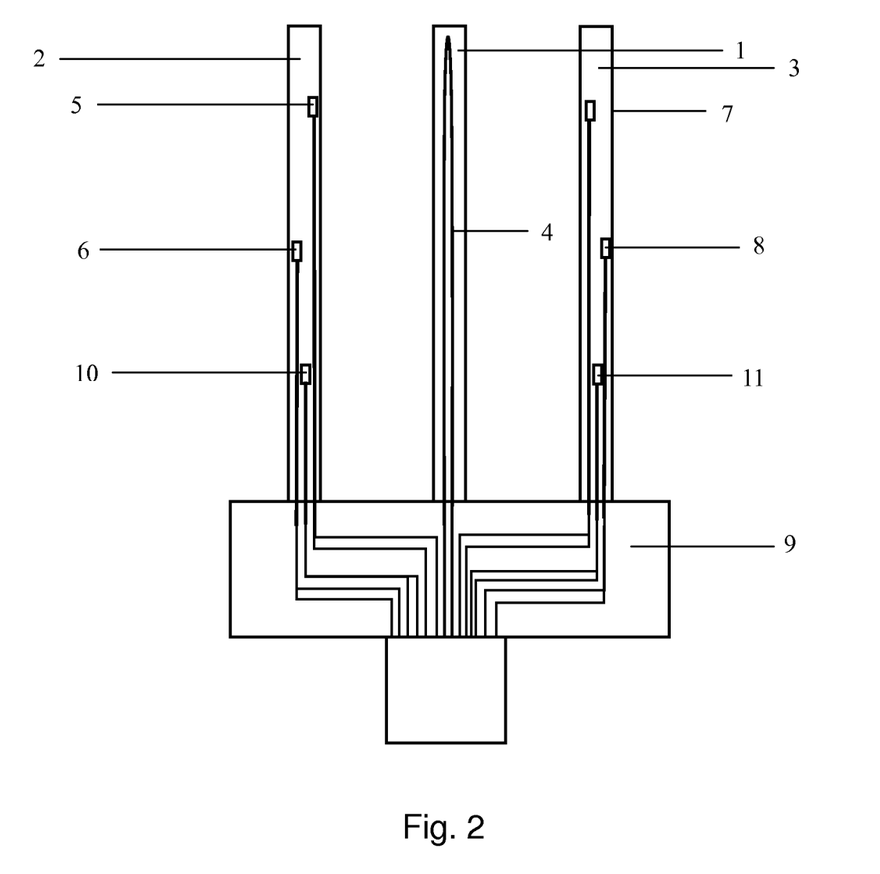
FIG. 2 is a sketch view of an in situ spacing-correcting heat pulse sensor for measuring sap flow or water flux according to a preferred embodiment of the present invention.

Referring to FIG. 2, an in situ spacing-correcting heat pulse sensor for measuring sap flow or water flux according to a preferred embodiment of the present invention is illustrated, wherein a quantity of thermometric elements is two if the temperature probe deflected inline and the quantity of thermometric elements is three if the temperature probe deflected not inline. The sensor comprises: a heating probe 1, a first temperature probe 2 and a second temperature probe 3 mounted on a holder 9, wherein the heating probe 1, the first temperature probe 2 and the second temperature probe 3 are all hollow needle tubes made of stainless steel or metal with higher thermal conductivity. A heating wire 4 made of nichrome (or other materials) is provided in the heating probe 1. A ratio of a length to a diameter of the heating probe 1 is larger than 25. Thermometric elements are mounted in the temperature probe: A first thermometric element 5 and a second thermometric element 6 are mounted in the first temperature probe 2 and a third thermometric element 7 and a fourth thermometric element 8 are mounted in the second temperature probe 3 when probes deflected inline. When probes deflected not inline, except the initial thermometric elements, a fifth thermometric element 10 and a sixth thermometric element 11 are also used in temperature probe 2 and 3 respectively. The heating probe 1 is connected to a DC power supply or battery. All the thermometric elements are respectively connected to a data collector. The thermometric element is thermistor, thermocouple, or other suitable thermometric elements. With the two or three thermometric elements in each of the first temperature probe 2 and the second temperature probe 3, according to a relative geometric relationship between the thermometric elements and the heating probe 1, the sensor is able to accurately obtain an actual spacing in field application after the temperature probes or the heating probe bends or deflected, and accurately obtain the sap flow and water flux, combined with other parameters.

In order to illustrate a design of the temperature probe, the first temperature probe 2 is taken as an example:

For increasing a noise-signal ratio, an axial spacing among thermometric elements (two elements for inline deflection, three elements for non-inline (nonlinear) deflection) is big enough along the first temperature probe 2, in such a manner that positions of the thermometric elements satisfy that: a relative deviation of a temperature, detected by the first or the second thermometric element (the third, for non-inline (nonlinear) deflection) arranged from a top or a bottom portion of the temperature probe, from a temperature detected at a middle position of the temperature probe, is less than 1%. With the above positions, not only is the noise-signal ratio increased, but also the measurement is accurate. For the sensor for measuring the soil water flux, the positions of the first thermometric element 5 and the third thermometric element 10 (for non-inline (nonlinear) deflection) in the first temperature probe 2 is illustrated in FIG. 2, wherein the thermometric elements are arranged along an axis of the temperature probe, and the thermometric elements are no less than 10 mm far from a top of the temperature probe and the holder 9. That is to say, the first thermometric element 5, which is near the top, is no less than 10 mm far from the top of the first temperature probe 2, and the second thermometric element 6 (or the third thermometric element 10 for non-inline (nonlinear) deflection), which is near the holder 9, is no less than 10 mm far from the holder 9. Furthermore, an axial distance between two adjacent thermometric elements is more than 6 mm for satisfying requirements. However, for measuring the sap flow in a plant, probe spacings as well as the axial distance between two adjacent thermometric elements are different under different conditions, and lengths of the probe are also different. Positions of the thermometric elements are determined before the in situ spacing correction. But in whatever cases, the positions of the thermometric elements satisfy that: a relative deviation of a temperature detected by the first, the second and the third (for non-inline (nonlinear) deflection) thermometric element arranged from a top or a bottom portion of the same temperature probe, from a given temperature detected at a middle position of the temperature probe, is less than 1%.

The heating probe 1, the first temperature probe 2 and the second temperature probe 3 are grouted onto the holder 9 with a solidifiable sealing material with sufficient electric insulation, in such a manner that the heating wire and the thermometric elements are accurately mounted in right positions and insulated from surroundings. Preferably, the sealing material is epoxy resin, or other suitable materials according to conditions. Besides, the quantity of the temperature probes is 1, 2 or more. As long as at least two thermometric elements are arranged in each of the temperature probe, the spacings are correctable according to the present invention.

Figure 3:
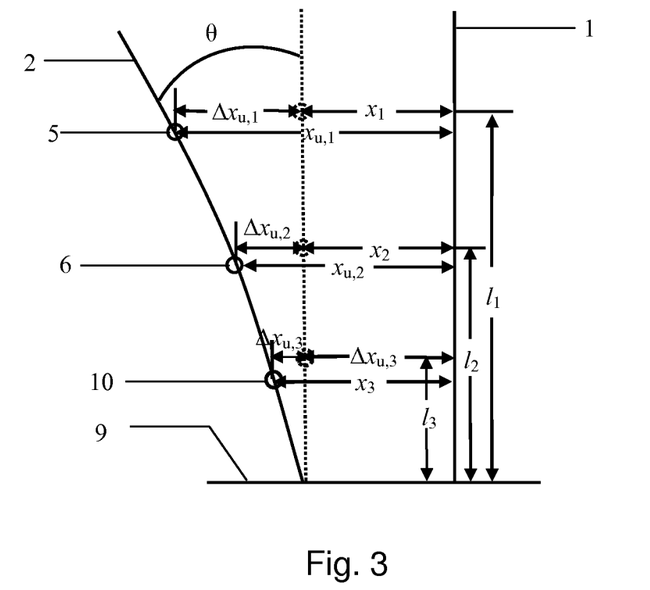
FIG. 3 is a sketch view of a temperature probe deflected non-inline (nonlinear) outwards according to the preferred embodiment of the present invention.

A measuring method of the above sensor is illustrated, which is able to correct the actual spacing between the temperature probe and the heating probe, wherein measuring the sap flow in trees is taken as an example, the method comprises steps of:

a) respectively calibrating the initial spacings from the first thermometric element 5, the second thermometric element 6, (the third thermometric element 10), the fourth thermometric element 7 and the fifth thermometric element 8 (the sixth thermometric element 11) in the first temperature probe 2 and the second temperature probe 3 to the heating probe 1, wherein a material whose thermal conductivity and specific heat are known is utilized for calibrating; for the first temperature probe 2, the calibrated initial spacings from the first thermometric element 5, the second thermometric element 6 and the third thermometric element 10 to the heating probe are respectively marked as $x_1$, $x_2$ and $x_3$;

b) drilling holes in a tree to be tested, and inserting the temperature probes and the heating probe into the holes in the tree; applying heat pulse when the sap flow in the tree is 0 or approximately 0, wherein heat released by the heating probe 1 is transmitted to the first temperature probe 2 and the second temperature probe 3, and the first thermometric element 5, the second thermometric element 6, (the third thermometric element 10), the fourth thermometric element 7, the fifth thermometric element 8, (the sixth thermometric element 11) in the first temperature probe 2 and the second temperature probe 3 respectively detect temperatures which change with time; and thus obtaining a first temperature-time response curve $\Delta T(t)\sim t$ which is recorded by the external data collector;

c) for inline deflection, judging whether the temperature probe deflects inwards or outwards according to a difference between temperature changes of the two thermometric elements (inside the same temperature probe), wherein if a time $t_{u,1}$ for the first temperature element 5 to reach a maximum value is longer than a time $t_{u,2}$ for the second temperature element 6 to reach a maximum value, the temperature probe deflects outwards; otherwise, the temperature probe deflects inwards and for non-inline deflection, directly executing a step d);

d) calculating the actual spacings between the temperature elements and the heating probe according to the data collected in the step b (the actual spacings from the first thermometric element 5, the second thermometric element 6 and the third thermometric element 10 in the first temperature probe 2 (regard as the upstream temperature probe) to the heating probe are respectively marked as $x_{u,1}$, $x_{u,2}$ and $x_{u,3}$, and the actual spacings from the fourth thermometric element 7, the fifth thermometric element 8 and the sixth thermometric element 11 in the second temperature probe 3 (regard as the downstream temperature probe) to the heating probe are respectively marked as $x_{d,1}$, $x_{d,2}$ and $x_{d,3}$), there are two conditions, inline deflection and not inline deflection, wherein:

Inline Deflection if the temperature probe is deflected inline, only two thermometric elements, (thermometric elements 5 and 6 for the temperature probe 2 or thermometric elements 7 and 8 for the temperature probe 3) in each temperature probe are used, and taking the first temperature probe 2 (the upstream temperature probe) as an example (we define $t_{u,1}$ as the time for the first temperature element 5 to reach a maximum value, $t_{u,2}$ as the time for the second temperature element 6 to reach a maximum value):

$\eta_1$ and $\eta_2$ are defined as:

$$\frac{\frac{1}{(t_{u,i}-t_0)}-\frac{1}{t_{u,i}}}{\ln\left[\frac{t_{u,i}}{(t_{u,i}-t_0)}\right]} = \eta_i, (i=1,2) \quad (17)$$

supposing that a wood (or soil) is homogeneous, thermal diffusivities $\alpha_1$ and $\alpha_2$ measured by the two thermometric elements in the temperature probe 2 are the same, according to the calculation method of thermal diffusivity in the theoretical background introduction of the present invention, namely the equation 16, a relationship of $\eta_1$ and $\eta_2$ is obtained, which is defined as:

$$\frac{x_{u,1}}{x_{u,2}} = \sqrt{\frac{\eta_2}{\eta_1}} = P \quad (18)$$

a specific method for calculating the theoretical deflection angle θ (inline deflection), the thermal diffusivity, and the actual spacings $x_{u,1}$ as well as $x_{u,2}$ are as follows:

the theoretical deflection angle θ (inline deflection) is calculated under the following conditions, wherein taking the first temperature probe 2 as an example, though based on inline deflections, the following equations are proved applicable no matter the temperature probe deflect, the heating probe deflect, both deflect or even non-inline deflected conditions:

Inline Deflection (Outward)

if the temperature probe is deflected outwards inline:

referring to FIG. 3, when the temperature probe 2 is deflected outwards inline, the above equations are specifically expressed as:

$$P = \frac{x_{u,1}}{x_{u,2}} = \frac{x_1 + l_1\sin\theta}{x_2 + l_2\sin\theta} \quad (19)$$

wherein $l_1$ and $l_2$ are respectively the distances from the first thermometric element 5 and the second thermometric element 6 to the holder 9; according to equation 19, the deflection angle θ is:

$$\theta = \sin^{-1}\left((-1)\frac{x_1 - x_2 P}{l_1 - l_2 P}\right) \quad (20)$$

for a given θ, the spacing changes between the deflected temperature probe and the heating probe are:

$$\Delta x_{u,i} = l_i \sin\theta, (i=1,2) \quad (21)$$

the actual spacings between the temperature elements of a deflected temperature probe and the heating probe are:

$$x_{u,i} = x_i + \Delta x_{u,i}, (i=1,2) \quad (22)$$

accordingly, the actual spacings from the first thermometric element 5 and the second thermometric element 6 of the deflected temperature probe to the heating probe 1 are:

$$x_{u,i} = x_i + l_i \sin\theta, (i=1,2) \quad (23)$$

Figure 4:
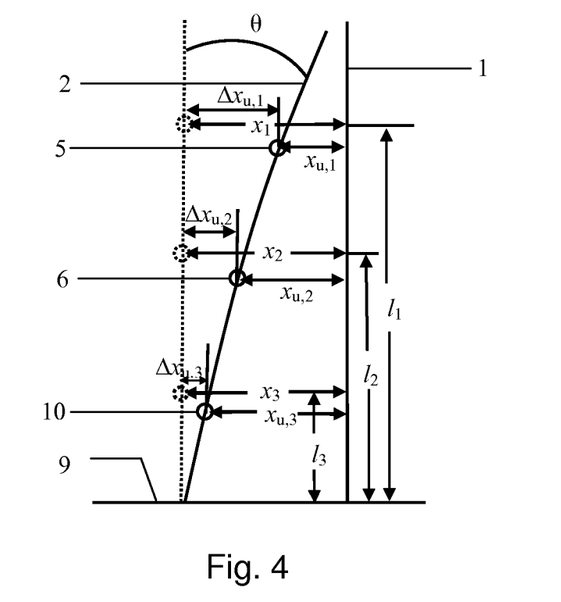
FIG. 4 is a sketch view of a temperature probe deflected non-inline (nonlinear) inwards according to the preferred embodiment of the present invention.

Inline Deflection (Inward)

if the temperature probe was deflected inwards inline:

the calculation method is basically the same as that of the temperature probe deflected outwards:

$$\theta = \sin^{-1}\left(\frac{x_1 - x_2 P}{l_1 - l_2 P}\right) \quad (24)$$

therefore:

$$x_{u,i} = x_i - \Delta x_{u,i}, (i=1,2) \quad (25)$$

accordingly, the actual spacings from the first thermometric element 5 and the second thermometric element 6 of the deflected temperature probe to the heating probe 1 are:

$$x_{u,i} = x_i - l_i \sin\theta, (i=1,2) \quad (26)$$

Non-Inline Deflection if the temperature probe was deflected not inline, i.e. nonlinear deflection, three thermometric elements (thermometric elements 5, 6 and 10 for the temperature probe 2 or thermometric elements 7, 8 and 11 for the temperature probe 3) in each temperature probe are used, and also as the inline deflection, taking the first temperature probe 2 (the upstream temperature probe) as an example, similarly to the inline deflection, we define $t_{u,1}$ as the time for the first temperature element 5 to reach a maximum value, $t_{u,2}$ as the time for the second temperature element 6 to reach a maximum value and $t_{u,3}$ is the time for the third temperature element 10 to reach a maximum value, then $\eta_1$, $\eta_2$ and $\eta_3$ can be defined as:

$$\frac{\frac{1}{(t_{u,i} - t_0)} - \frac{1}{t_{u,i}}}{\ln\left[\frac{t_{u,i}}{(t_{u,i} - t_0)}\right]} = \eta_i, (i = 1, 2, 3) \tag{27}$$

just as the case of two thermometric elements, supposing that a wood (or soil) is homogeneous, thermal diffusivities $\alpha_1$, $\alpha_2$ and $\alpha_3$ measured by the three thermometric elements in the temperature probe 2 should be the same:

$$\frac{x_{u,1}^2}{4}\eta_1 = \frac{x_{u,2}^2}{4}\eta_2 = \frac{x_{u,3}^2}{4}\eta_3 \tag{28}$$

and therefore relationships of $\eta_1$, $\eta_2$ and $\eta_3$ can also be expressed as:

$$\frac{x_{u,1}}{x_{u,2}} = \sqrt{\frac{\eta_2}{\eta_1}} = P_1; \frac{x_{u,2}}{x_{u,3}} = \sqrt{\frac{\eta_3}{\eta_2}} = P_2 \tag{29}$$

when the deflection is not inline, the spacing changes $\delta x_{u,1}$, $\delta x_{u,2}$ and $\delta x_{u,3}$ can be approximated as:

$$\delta x_{u,i} = a l_i + b l_i^2, (i=1,2,3) \tag{30}$$

wherein $l_1$, $l_2$ and $l_3$ are respectively the distances from the first thermometric element 5, the second thermometric element 6, the third thermometric element 10 to the holder 9, and $\delta x_{u,1}$, $\delta x_{u,2}$ and $\delta x_{u,3}$ satisfy:

$$|\delta x_{u,i}| = \Delta x_{u,i}, (i=1,2,3) \tag{31}$$

when the temperature probe was deflected outwards not inline, $\delta x_{u,1}$, $\delta x_{u,2}$ and $\delta x_{u,3}$ were positive numbers and when the temperature probe was deflected outwards not inline, $\delta x_{u,1}$, $\delta x_{u,2}$ and $\delta x_{u,3}$ were negative numbers, thus:

$$x_{u,i} = x_i + \delta x_{u,i} = \Delta x_i \pm \Delta x_{u,i}, (i=1,2,3) \tag{32}$$

wherein, "+" is used for the outward not inline (nonlinear) deflected conditions, and "−" is used for the inward not inline (nonlinear) deflected conditions;

according to equations 29, 30 and 32, we have $$\frac{x_1 + a l_1 + b l_1^2}{x_2 + a l_2 + b l_2^2} = P_1; \frac{x_2 + a l_2 + b l_2^2}{x_3 + a l_3 + b l_3^2} = P_2 \tag{33}$$

a system of equations in the two variables a and b could get from equation 33:

$$\begin{cases} a(l_1 - l_2 P_1) + b(l_1^2 - l_2^2 P_1) + x_1 - x_2 P_1 = 0 \\ a(l_2 - l_3 P_2) + b(l_2^2 - l_3^2 P_2) + x_2 - x_3 P_2 = 0 \end{cases} \tag{34}$$

define $l_1 - l_2 P_1$ as $\zeta_1$, $l_1^2 - l_2^2 P_1$ as $\beta_1$, $x_1 - x_2 P_1$ as $\chi_1$, $l_2 - l_3 P_2$ as $\zeta_2$, $l_2^2 - l_3^2 P_2$ as $\beta_2$, $x_2 - x_3 P_2$ as $\chi_2$, respectively; then, equation 34 can be simplified as:

$$\begin{cases} a\zeta_1 + b\beta_1 + \chi_1 = 0 \\ a\zeta_2 + b\beta_2 + \chi_2 = 0 \end{cases} \tag{35}$$

then the solution is:

$$a = \frac{\beta_1 \chi_2 - \beta_2 \chi_1}{\zeta_1 \beta_2 - \zeta_2 \beta_1}; b = \frac{\zeta_2 \chi_1 - \zeta_1 \chi_2}{\zeta_1 \beta_2 - \zeta_2 \beta_1} \tag{36}$$

when b=0, the non-inline deflection (nonlinear deflection) reduces to the inline deflection. The inline deflection method can also be used as the first order approximation for the condition of non-inline deflection (nonlinear deflection);

e) obtaining $x_{d,1}$, $x_{d,2}$ and $x_{d,3}$ of the second temperature probe 3 (the downstream temperature probe) in the same way;

f) sampling a second temperature-time response data when the sap flow in the tree is not 0; and g) calculating the sap flow in the tree according to parameters comprising the actual spacings ($x_{u,1}$, $x_{d,1}$, $x_{u,2}$, $x_{d,2}$, $x_{u,3}$ and $x_{d,3}$) from the thermometric elements in the temperature probe to the heating probe, and the times for temperatures of the two or three (for non-inline (nonlinear) deflection) thermometric elements to reach maximum values or other parameters.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An in situ spacing-correcting heat pulse sensor for measuring sap flow or water flux, comprising:
a holder;
a temperature probe or two or no less than two mounted on said holder; and
a heating probe mounted on said holder;
wherein two thermometric elements for inline deflection or three thermometric elements for non-inline deflection are provided axially in said same temperature probe, said all thermometric elements are connected to a data collector, a heating wire is mounted in said heating probe, and said heating wire is connected to a DC power supply or battery.

2. The sensor, as recited in claim 1, wherein a ratio of a length to a diameter of said heating probe is larger than 25.

3. The sensor, as recited in claim 1, wherein positions of said first and said second or a third thermometric elements in said temperature probe satisfy that: a relative deviation of a temperature detected by a first, a second or a third thermometric element arranged from a top or a bottom portion of said temperature probe, from a temperature detected at a middle position of said temperature probe, is less than 1%.

4. The sensor, as recited in claim 1, wherein a quantity of said temperature probe is no less than 1.

5. The sensor, as recited in claim 1, wherein said temperature probe and said heating probe are grouted onto said holder with a sealing material which is insulating and solidifiable.

6. The sensor, as recited in claim 5, wherein said sealing material is epoxy resin or all any other suitable material with high thermal conductivity.

7. The sensor, as recited in claim 1, wherein said temperature probe and said heating probe are both hollow needle tubes made of metal with high thermal conductivity, preferably, stainless steel.

8. A measuring method of an in situ spacing-correcting heat pulse sensor for measuring sap flow or water flux, comprising steps of:
   a) respectively calibrating initial spacings between two thermometric elements for inline deflection or three thermometric elements for non-inline deflection in a temperature probe and a heating probe;
   b) when soil water flux or sap flow in a tree is 0 or approximately 0, inserting the temperature probe and the heating probe into the soil or pre-drilled holes in the tree, and sampling a first temperature-time response data;
   c) for the inline deflection, judging whether the temperature probe is deflected inwards or outwards according to a difference between temperature changes of the two thermometric elements in the same temperature probe, wherein if a time $t_{u,1}$ for a temperature of the first thermometric element to reach a maximum value is longer than a time $t_{u,2}$ for a temperature of the second thermometric element to reach a maximum value, the temperature probe deflected outwards; otherwise, the temperature probe deflected inwards; and for the non-inline deflection, directly executing a step d);
   d) calculating the actual spacings between the thermometric elements and the heating probe after the temperature probe or the heating probe deflects, and calculating a thermal diffusivity;
   e) sampling a second temperature-time response data when the sap flow in the tree or the water flux in the soil is not 0; and
   f) calculating the sap flow in the tree or the water flux according to parameters comprising the calculated actual spacings and times for temperatures of the two thermometric elements for the inline deflection or the three thermometric elements for the non-inline deflection in the temperature probe to reach maximum values.

9. The method, as recited in claim 8, wherein the initial spacings between the two or three thermometric elements in the temperature probe and the heating probe are calibrated with a material whose heat conductivity and specific heat are known.

* * * * *